United States Patent [19]

Sakuma et al.

[11] Patent Number: 4,996,985
[45] Date of Patent: Mar. 5, 1991

[54] DEFIBRILLATOR WITH CORD STORAGE SUPPORT MEANS

[75] Inventors: Hisayoshi Sakuma; Isamu Ishihara, both of Tokyo, Japan

[73] Assignee: Fukuda Denshi Co., Ltd., Tokyo, Japan

[21] Appl. No.: 473,525

[22] Filed: Feb. 1, 1990

[30] Foreign Application Priority Data

Aug. 15, 1989 [JP] Japan .................. 1-95704[U]

[51] Int. Cl.[5] .............................................. A61N 1/39
[52] U.S. Cl. .................. 128/419 D; D24/8; D24/29
[58] Field of Search ............... 128/419 D, 420–424; D24/1.001, 7, 8, 17, 29, 99

[56] References Cited

U.S. PATENT DOCUMENTS

| 282,431 | 7/1883 | Andrews et al. | 128/419 R |
| 1,482,891 | 2/1924 | Ghegan | 128/423 |
| 4,023,573 | 5/1977 | Pantridge et al. | 128/419 D |

Primary Examiner—William E. Kamm
Attorney, Agent, or Firm—Sughrue, Mion, Zinn, Macpeak and Seas

[57] ABSTRACT

First and second support members 6, 7 are mounted intermediate the opposite ends of elongate, helically curled stretch cords 4, 5 connecting the defibrillator electrodes 2, 3 to an apparatus housing 1. Such first members are retentively engaged by second support members 8, 9 on the sides of the housing such that the cord bights, when the apparatus is not in use, lie against the housing wherefrom they are readily releasable by removing the electrodes and pulling on them.

5 Claims, 3 Drawing Sheets

DEFIBRILLATOR WITH CORD STORAGE SUPPORT MEANS

BACKGROUND OF THE INVENTION

This invention relates to a defibrillator apparatus for treating a patient in an urgent or extremis situation, embodying means for releasably storing the electrode cords against the sides of the apparatus housing.

When a heart stoppage or ventricular fibrillation occurs, it is essential that the patient be immediately treated to prevent death. Such treatment typically involves applying the two electrodes of a defibrillator apparatus to the breast of the patient, and applying a high voltage pulse to the patient through the electrodes to stimulate the heart to resume its pumping action. In such extremis situations, it is essential that the electrodes, which are connected to the defibrillator apparatus housing by elongate, helically curled cords, be readily and immediately removable from their stored position such that they can be quickly brought into engagement with the patient.

Several prior art arrangements are illustrated in the partial perspective views of Figs. 1A, 1B and 1C. In the arrangement of Fig. 1A. an electrode 105 of a defibrillator 100 is connected thereto by an elongate, curled "stretch" cord 104, whose bight is stored against a side 101 of the defibrillator housing by engagement in a pair of trough-like holders 102. 103. With this arrangement, however, the operator must independently disengage the cord from both of the holders, which involves an unacceptable loss of time in the emergency conditions under which defibrillators are used. A simple pulling on the cord will not suffice, as its curls or turns can easily become entangled in the retention hooks at the ends of the holders.

In the arrangement of Fig. 1B. the cord 104, when not in use, is wrapped around the electrode 105, while in the arrangement of Fig. 1C, the cord bight is simply left hanging down. In the former case, the cord can easily become entangled with the electrode itself when the electrode is rapidly removed for use in an emergency situation, while in the latter case, the suspended or hanging bight of the cord can easily become caught on surrounding equipment and pulled loose from the housing or the electrode when the electrode is rapidly removed and manipulated.

SUMMARY OF THE INVENTION

The present invention avoids the drawbacks and disadvantages of the prior art discussed above by providing a defibrillator apparatus wherein the electrode cords are releasably stored, when not in use, against the opposite sides of the apparatus housing in such a manner that they can be quickly and easily released from their stored positions by simply removing the electrodes from their rest positions and pulling on the cords, all in one operation and without having to independently remove the cords from their stored positions.

DETAILED DESCRIPTION OF THE PREFERRED EMBODIMENTS

Figure 1A:
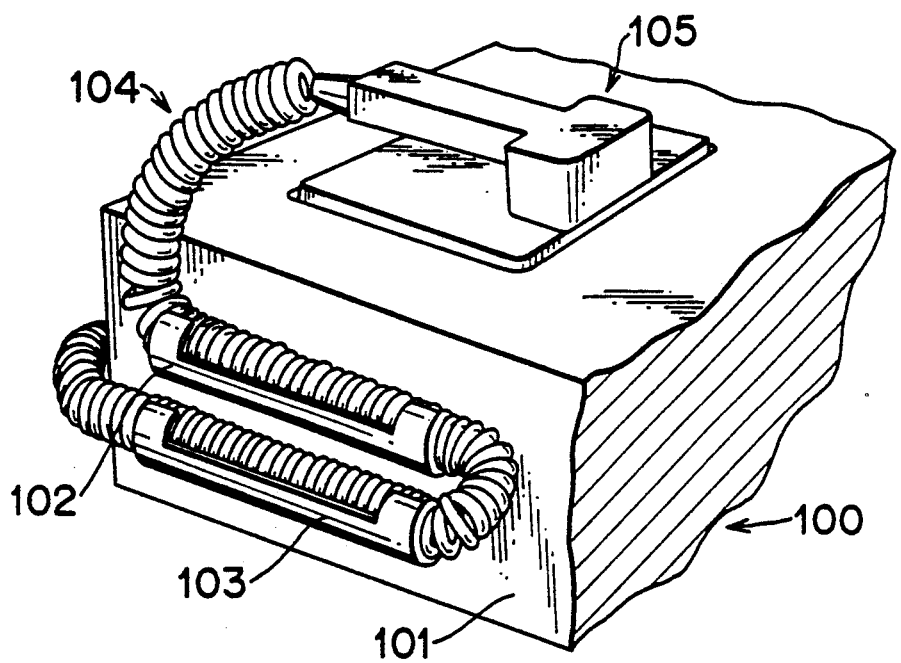
FIGS. 1A, 1B and 1C are partial perspective views showing various prior art arrangements for storing the electrode cords of a defibrillator apparatus.
Figure 1B:
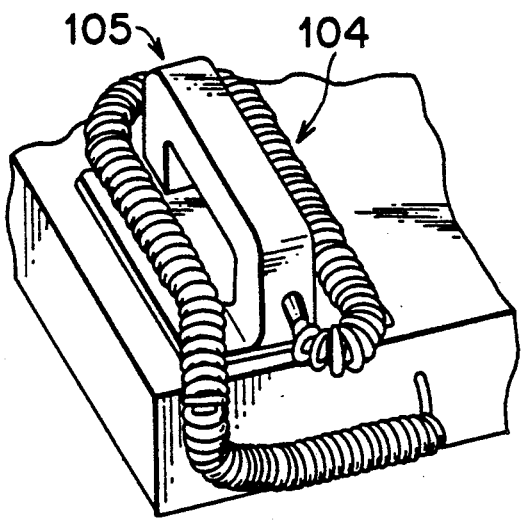
Figure 1C:
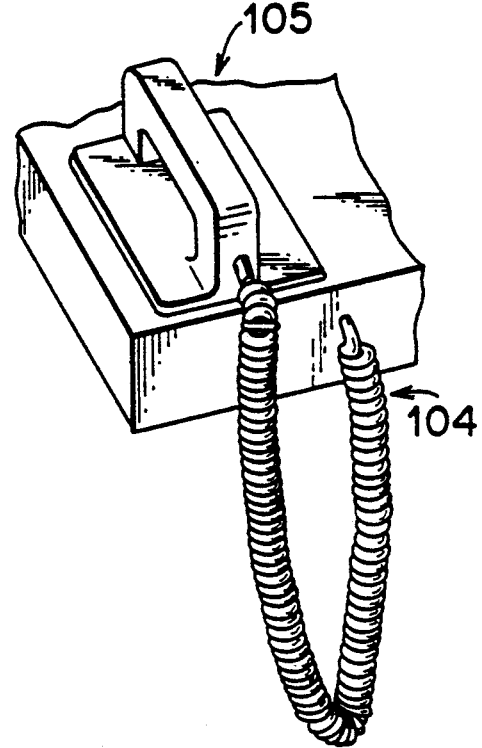
Figure 2:
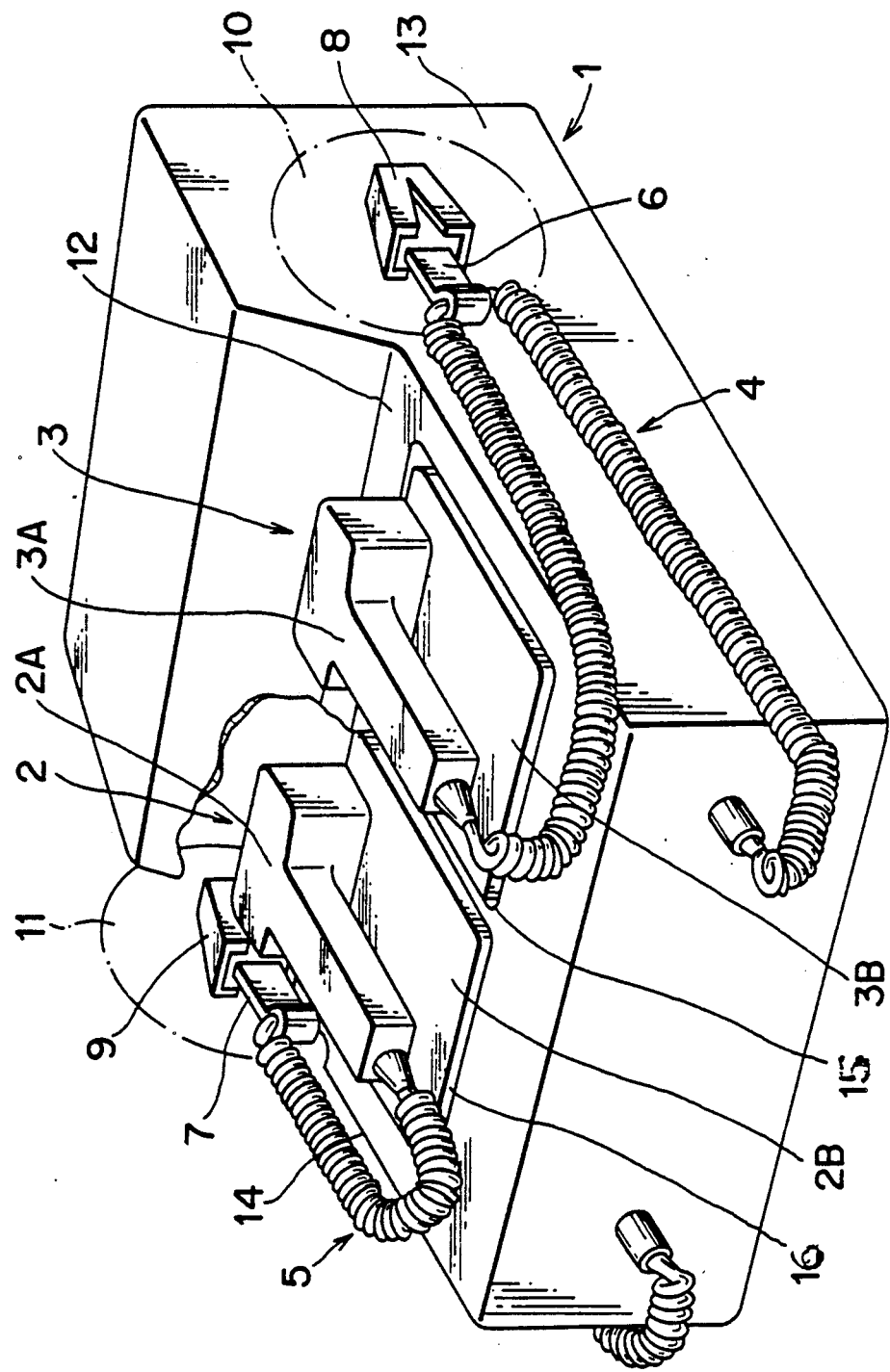
FIG. 2 is a perspective view showing a defibrillator apparatus according to a first embodiment of the present invention.

Referring to FIG. 2, reference numeral 1 designates a defibrillator apparatus housing, 2 and 3 are electrodes in their rest or stored positions. 4 and 5 are elongate helically curled cords connecting the respective electrodes to the apparatus housing, 6, 7 and 8, 9 designate first and second cord support members, respectively, and 10 and 11 designate cord storage areas or zones on the respective sides 13 and 14 of the apparatus housing.

The apparatus housing may be made of plastic, for example, and its upper surface 12 defines recesses 15, 16 in which the electrodes are seated or stored when not in use. The electrodes comprise patient contact plates 2B, 3B connected to handgrips 2A, 3A, and the cords 4, 5 are connected to the outermost ends of the handgrips. The first cord support members 6, 7 are mounted intermediate the opposite ends of the cords 4, 5, and the second cord support members 8, 9 are mounted on the sides of the apparatus housing in the support zones 10, 11 at the rear areas of the housing sides 13, 14.

Figure 3A:
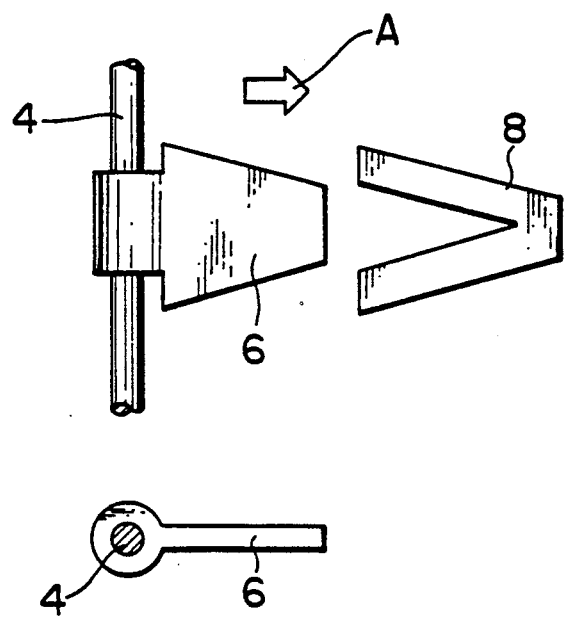
FIG. 3A is a detailed illustration of the cord storage members of the first embodiment.

Referring to FIG. 3A, according a first embodiment of the invention, the first cord support member 6 is formed by a rubber plate, and the second cord support member 8 is formed by a complementary shaped holder in which the rubber plate may be removably accommodated. The rubber plate surrounds the cord 4 and is bonded to it, as shown in the lower portion of 3A. The second cord support member 8 or holder, on the other hand, may be integrally formed with the apparatus housing.

Figure 3B:
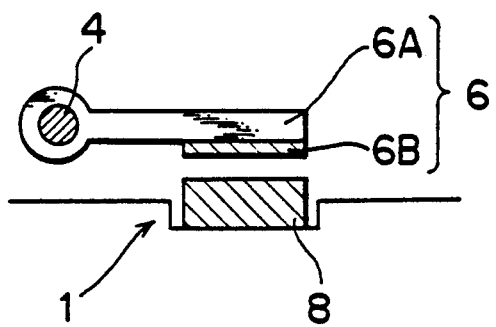
FIG. 3B is a detailed view of the cord storage members according to a second embodiment of the invention.

In the second embodiment illustrated in FIG. 3B, the first cord support member 6 is formed by a plate 6A carrying an iron segment 6B, and the second cord support member 8 is formed by a magnet mounted in a recess of the apparatus housing, and adapted to attract the iron segment 6B. The plate 6A may be made of leather or cloth, and surrounds the cord 4 and is bonded to it just as in the first embodiment.

The second embodiment is more efficient than the first embodiment in an urgent situation, as the cords 4 and 5 may be readily removed from their stored positions by simply pulling on them to break the magnetic retention of the iron segments against the magnets.

In operation, when the apparatus is not in use, the electrodes 2, 3 are stored in their respective recesses 16, 15, and the first cord support members 6, 7 are frictionally inserted into their respective second cord support members 8, 9 by pushing them in the direction of arrow A in FIG. 3A. When the electrodes are removed for emergency use by a doctor or technician, the handgrips 2A, 3A are seized and pulled away from the housing 1. The forces resulting from such pulling quickly disengage the first and second cord support members, whereby the electrodes may be freely and rapidly brought into engagement with the breast of the patient.

Since the bights of the cords 4, 5, when the apparatus is not in use, are conveniently stored against the sides of the housing 1 "out of harms way", they are not susceptible to becoming entangled with or hung up against any nearby projections or other equipment, whereby the apparatus is always in a condition for rapid emergency use.

We claim:

1. A defibrillator apparatus for treating a patient wherein first and second elongate, helically curled cords connect, respectively, first and second electrodes with a housing of the apparatus, comprising:

a pair of first cord support members (6,7) individually mounted on said first and second cords (4,5) intermediate opposite ends thereof; and a pair of second cord support members (8,9) individually mounted on said apparatus housing, and adapted to retentively engage said first cord support members;

said cords being stored against the apparatus housing by engagement between the first and second cord support members and being readily and easily releasable from storage by pulling on the cords to enable the use of the apparatus.

2. An apparatus according to claim 1, wherein said second cord support members are mounted, respectively, at rear areas of right and left side surfaces of said apparatus housing.

3. An apparatus according to claim 1, wherein said first cord support members are plates made of rubber, and said second cord support members are holders in which said plates are individually accommodated.

4. An apparatus according to claim 1, wherein said first cord support members are composed of plates and iron segments affixed to said plates, and said second cord support members are formed by magnets capable of attracting said iron segments.

5. An apparatus according to claim 4, wherein said plates are formed by leather or cloth.

* * * * *